(12) United States Patent
Eby

(10) Patent No.: US 8,550,982 B2
(45) Date of Patent: Oct. 8, 2013

(54) CLOSED-CHEST STABILIZATION SYSTEM AND METHODS FOR MINIMALLY INVASIVE HEART SURGERY

(75) Inventor: Thomas B. Eby, Mountain View, CA (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 853 days.

(21) Appl. No.: 12/640,628

(22) Filed: Dec. 17, 2009

(65) Prior Publication Data

US 2010/0160720 A1   Jun. 24, 2010

Related U.S. Application Data

(60) Provisional application No. 61/139,243, filed on Dec. 19, 2008.

(51) Int. Cl.
*A61F 2/00* (2006.01)
(52) U.S. Cl.
USPC .......................................................... 600/37
(58) Field of Classification Search
USPC ............. 600/37, 422; 606/143–144; 623/2.1
See application file for complete search history.

(56) References Cited

U.S. PATENT DOCUMENTS

| 4,994,042 | A | 2/1991 | Vadher |
| 5,328,482 | A | 7/1994 | Sircom et al. |
| 5,676,658 | A | 10/1997 | Erskine |
| 6,551,278 | B1 | 4/2003 | Geitz |
| 6,749,588 | B1 | 6/2004 | Howell et al. |
| 7,112,219 | B2 * | 9/2006 | Vidlund et al. ................ 623/2.1 |

* cited by examiner

*Primary Examiner* — Christine Matthews
(74) *Attorney, Agent, or Firm* — Trenner Law Firm, LLC

(57) ABSTRACT

Stabilization systems and methods for various procedures (e.g., tissue ablation procedures) are disclosed. An exemplary stabilization system for use in a medical procedure may include a housing structure having a base portion, the housing structure insertable into a patient's body. The system may also include a securement element on the base portion of the housing structure. The system may also include a deployment mechanism in the housing structure and operably associated with the base portion. The deployment mechanism is operable to extend the base portion so that the at least one securement element engages a tissue in the patient's body after the housing structure is positioned adjacent a target area inside a patient's body. Embodiments of the securement element may include a membrane, a chamber, a frictional surface, at least one needle, peg, gasket, adhesive, and/or a collar.

15 Claims, 9 Drawing Sheets

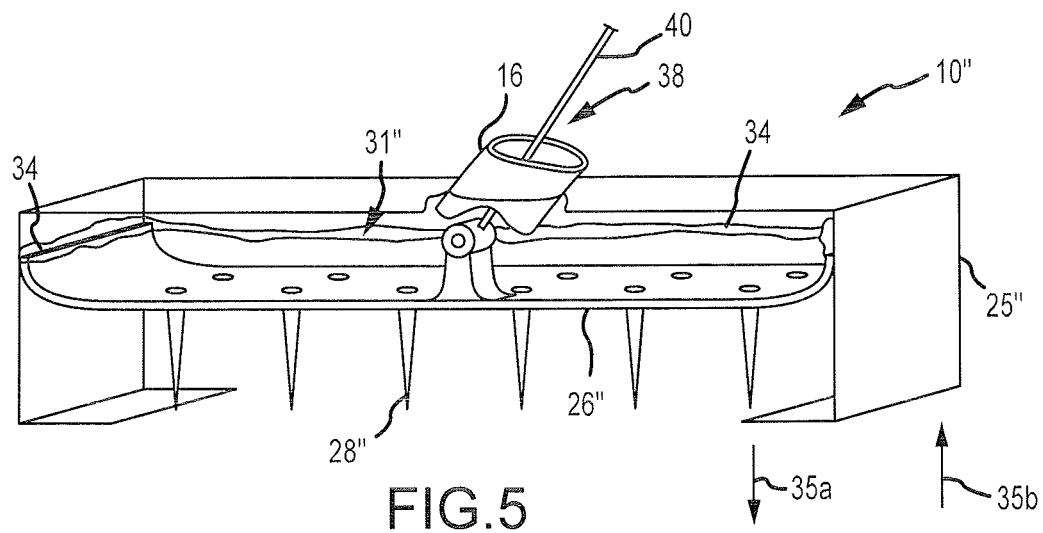
FIG.5
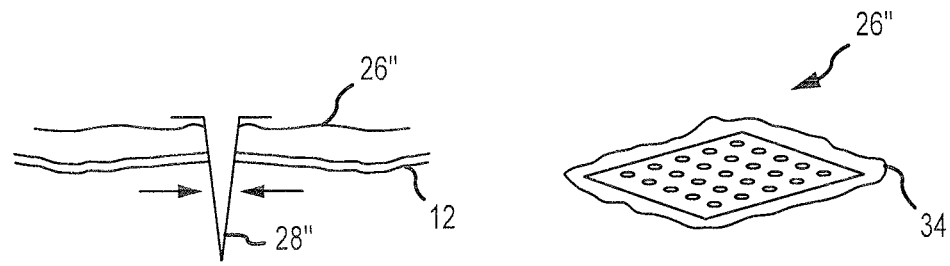
FIG.6b
FIG.6a

CLOSED-CHEST STABILIZATION SYSTEM AND METHODS FOR MINIMALLY INVASIVE HEART SURGERY

CROSS REFERENCE

The present application claims priority to U.S. Provisional Patent Application No. 61/139,243, filed 19 Dec. 2008, which is incorporated by reference herein in its entirety.

BACKGROUND OF THE INVENTION a. Field of the Invention

This disclosure relates to a medical device stabilization system and methods for use (e.g., for minimally invasive heart surgery) for a wide variety of devices such as an ablation catheter which may be temporarily anchored to or biased toward an organ or the targeted tissue of the organ for medical procedures.

b. Background Art

Normal heart rhythm is between 60 and 100 beats per minute. Tachycardia is a fast heart rate (usually over 100 beats per minute) caused by disease or injury. Tachycardias may begin in the upper chambers of the heart (the atria) or the lower chambers of the heart (the ventricles). Some tachycardias are harmless, but other tachycardias are life threatening. With this disorder, the heart does not fill with enough blood between beats to meet the needs of the body. Tachycardias can quickly deteriorate to fibrillation.

Atrial fibrillation (AF) is the most common abnormal heart rhythm. It is a very fast, uncontrolled heart rhythm that occurs when the upper chambers of the heart (the atria) try to beat so fast (between 350 and 600 times per minute) that they only quiver and fail to effectively pump blood to the organs and other tissues of a subject. Ventricular fibrillation (VF) occurs when the lower chambers of the heart (the ventricles) produce impulses that make the heart beat too quickly. Fibrillation is a life-threatening arrhythmia demanding immediate treatment.

Before a tachycardia deteriorates to fibrillation, various procedures may be used to treat the heart tissue and reduce or altogether eliminate the occurrence of fibrillations. It is well known that treatment benefits may be gained by forming lesions in tissue if the depth and location of the lesions being formed can be controlled. These lesions block the errant electrical signals that result in the tachycardia. In particular, it can be desirable to elevate tissue temperature until thermally necrosed lesions are formed which change, i.e. reduce or eliminate the electrical conductivity of the tissue. For example, when "adequate" or "sufficiently deep" lesions are formed at specific locations in cardiac tissue, undesirable fibrillations may be permanently reduced or eliminated. The definition of "adequate" or "sufficiently deep" when describing lesion formation depends at least to some extent on the procedure and may also depend on other considerations, such as tissue characteristics and desired results. In general it is currently thought that transmural lesions are desired (i.e., lesions extending between the endocardium and the epicardium). However some recently reported work demonstrates this may not always be true.

Several difficulties may be encountered with existing ablation or lesion-making techniques. For example, during minimally invasive surgical (MIS) ablation procedures on a patient's heart, a physician makes a small incision in the patient's abdomen for insertion of an ablation device. The ablation device may have a high intensity focused ultrasound (HIFU) electrode on the tip for delivering ablative energy to the heart tissue. The physician must maneuver the tip of the ablation device adjacent the heart tissue to be ablated (the "target tissue"). The physician may determine placement of the ablation device based on his/her experience maneuvering the ablation device during the ablation procedure. Such experience only comes with time, and may be quickly lost if the physician does not perform ablation procedures on a regular basis. In the case of MIS procedures the target tissue is not in the surgeon's direct line of sight.

Even an experienced physician may find it difficult to maneuver the ablation device. For example, an extended ablation device inserted through a small incision in the patient's abdomen severely limits the physician's ability to manipulate the tip of the ablation device in the desired direction near or on the heart. In addition, the axis of the ablation device may not be aligned with the desired lesion axis, thereby requiring the physician to reposition the ablation device so that the physician can pull the ablation device in the direction needed to form a linear or curvilinear lesion. Even after properly positioning the ablation device, it is often difficult to drag the ablation device at a constant velocity and at the appropriate angle to achieve a uniformly deep and wide lesion.

When these procedures are performed on the heart, the beating heart further complicates matters by making it difficult to assess placement of the ablation device adjacent the tissue during the time needed to form the desired lesion. That is to say that one would not want the ablation device moving uncontrollably, as by random lateral slippage or sliding, during the procedure. If the ablation device is not properly controlled, a quality lesion is unlikely to be formed and the procedure may be unsuccessful, needing to be repeated to achieve the desired result. In addition, there may be undesirable damage to the surrounding tissue.

Thus, there remains a need for controlled placement of a stationary or otherwise fixed ablator (relative to the tissue to be ablated) for ablation procedures.

BRIEF SUMMARY OF THE INVENTION

It is desirable to be able to control placement of ablation means and other devices during various procedures. This can be accomplished with the stabilization system according to the description, claims and drawings of the present disclosure.

The foregoing may be implemented in a stabilization system that biases, stabilizes or temporarily anchors an ablation element adjacent the target tissue during a medical procedure (e.g., ablation procedures). In one embodiment, one or more ablation elements may be positioned on or near the tissue using conventional techniques, such as, various position, orientation, and/or localization systems (e.g., EnSite system operating with NavX or the EnSite Velocity system from St. Jude Medical, Inc. of Little Canada, Minn. or the MediGuide magnetic system also from St. Jude Medical), fluoroscopy or ultrasound imaging, an optical scope, radiopaque markers, etc. Once positioned, the stabilization system is activated so that the ablation element(s) remain stationary relative to the tissue adjacent the target area, and the ablation element is used to perform the desired procedure in a controlled manner, e.g., enabling a physician to form quality lesions during ablation procedures.

In an exemplary embodiment of the present invention, the stabilization system for use in a medical procedure comprises a housing structure having a base portion, the housing structure insertable into a patient's body. A securement element is provided on the base portion of the housing structure. A deployment mechanism in the housing structure and operably associated with the base portion. The deployment mechanism is operable to extend the base portion so that the at least one securement element engages a volume of tissue in the patient's body after the housing structure is positioned adjacent a targeted tissue area inside a patient's body.

The present invention also includes a stabilization system for use in a medical procedure comprising a housing structure insertable through a catheter lumen or directly and manually into a patient's body, and a base portion of the housing structure. The base portion is moveable between a first position and a second position. A securement element is provided on the base portion of the housing structure. The securement element including an actuating mechanism and an engagement surface. A first deployment mechanism is provided in the housing structure. The first deployment mechanism is operable to extend the base portion so that the securement element engages a tissue in the patient's body. The first deployment mechanism is also operable to retract the base portion so that the securement element disengages the tissue in the patient's body. A collar is provided between the housing structure and a distal portion of the catheter, the collar including at least one tissue engaging member (e.g., a needle, a peg, a friction-inducing material, etc.). A second deployment mechanism is operably associated with the collar. The second deployment mechanism operable to extend the at least one tissue engaging member in the collar to engage the targeted tissue in the patient's body. The second deployment mechanism is also operable to retract the at least one tissue engaging member in the collar to disengage the housing from the targeted tissue in the patient's body.

The present invention also includes methods. In an exemplary embodiment, a method of treatment comprises: positioning a structure adjacent a targeted target area inside a patient's body, the structure including a securement element having at least one tissue engaging member deploying the member of the securement element to bias, stabilize and/or temporarily anchor the structure to a tissue in the targeted target area; and disengaging the member of the securement element from the targeted tissue following a medical procedure.

The stabilization system may also include an elongate member which provides a conduit to the housing structure. The elongate member couples to the ablation element (e.g., for delivering ablative or other therapeutic energy, receiving sensor signals, and delivering fluids and/or gases and the like via one or more lumens). The elongate member may also provide positive and negative pressure for delivering and/or receiving cooling fluid, flushing fluid, or other fluids, gels and/or a gas to controllably inflate and deflate one or more inflatable members coupled to a portion of the housing, including opposing portions of said housing.

The foregoing and other aspects, features, details, utilities, and advantages of the present invention will be apparent from reading the following description and claims, and from reviewing the accompanying drawings.

BRIEF DESCRIPTION OF THE DRAWINGS

FIG. 5 is a cutaway perspective view of another embodiment of an exemplary stabilization system having an exemplary safety mechanism.

FIG. 6a is a detailed perspective view of an exemplary base portion with edge seal which may be implemented in the stabilization system of FIG. 5.

FIG. 6b is a detailed plan view of a needle which may be implemented in the base portion of the stabilization system of FIG. 5.

DETAILED DESCRIPTION OF THE INVENTION

Several embodiments of a stabilization system according to the present invention are depicted in the figures as the stabilization system may be used for lesion formation or other medical procedures. As described further below, the stabilization system of the present invention provides a number of advantages, including, for example, the ability to control and maintain tissue contact and registration during lesion formation on targeted tissue. Tissue contact herein means positional registration and temporary coupling of the housing of one or more ablation elements to the targeted tissue, as well as other types of contact (e.g., acoustic contact or coupling of the ablation energy in the tissue). The stabilization system facilitates more reliable lesion formation, particularly in difficult environments (e.g., the tissue of a beating heart).

Before continuing, it is noted that other components typical of ablation systems which are conventionally implemented for such procedures, are not shown or described herein for purposes of brevity. Such components may nevertheless also be provided as part of, or for use with, the stabilization system. For example, medical devices for surgical procedures on the heart are commonly used in conjunction with an ECG recording system, associated sensing and/or pacing electrodes, and/or various input and output devices. Such components are well understood in the medical devices arts and therefore further explanation is not necessary for a complete understanding of the invention.

Figure 1A:
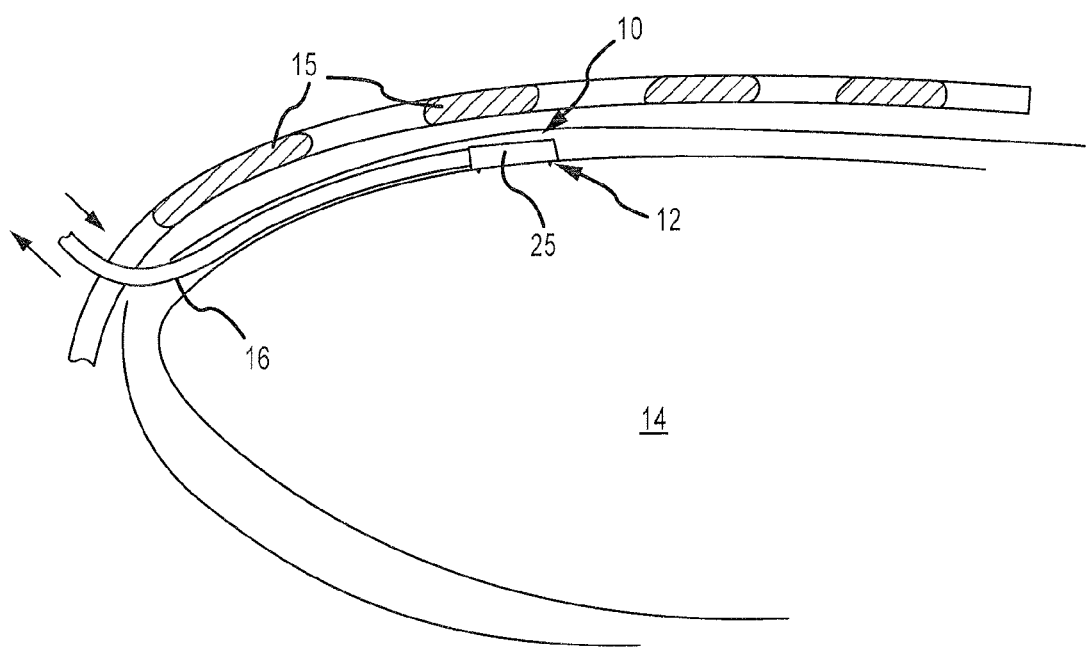
FIG. 1a-b are high level illustrations showing an exemplary embodiment of a stabilization system as it may be used in a patient's body for minimally invasive heart surgery, wherein (a) shows the stabilization system positioned adjacent a target area, and (b) shows a close-up view of the stabilization system after actuation.
Figure 1B:
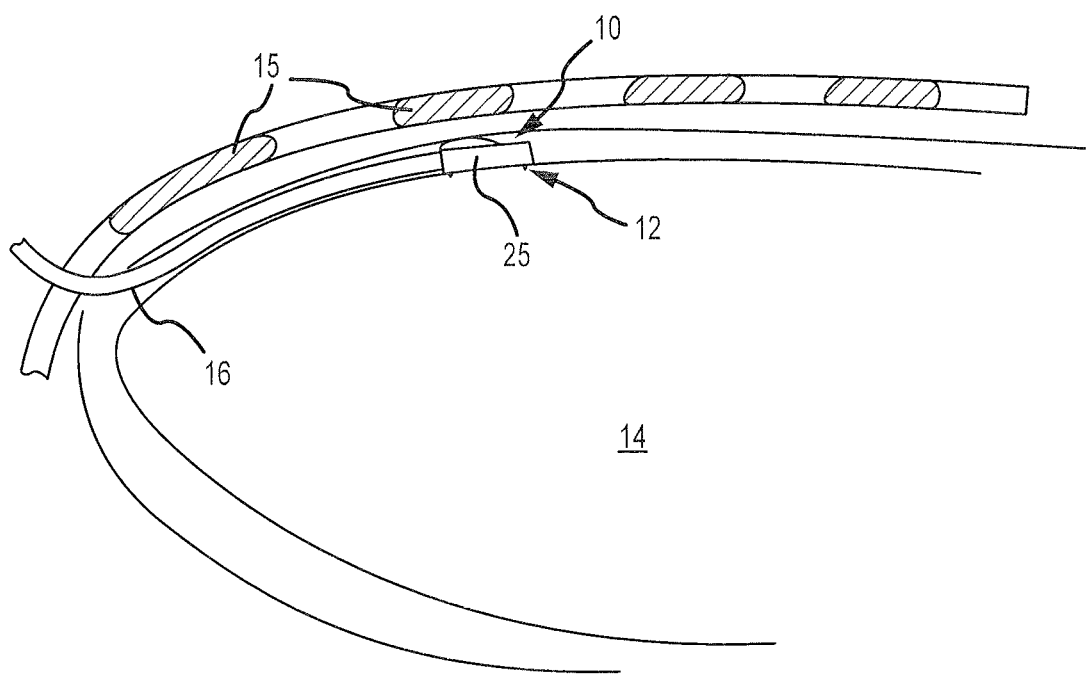
Figure 2:
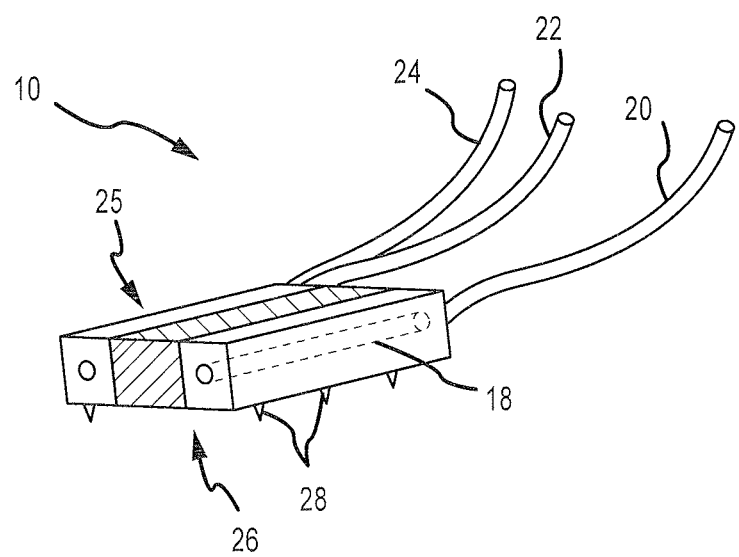
FIG. 2 is an isometric view of an exemplary stabilization system.

FIG. 1a-b are high level illustrations showing an exemplary embodiment of a stabilization system 10 as it may be used in a patient's body for minimally invasive heart surgery, wherein (a) shows the stabilization system 10 positioned adjacent a target area 12, and (b) shows the stabilization system 10 after it has been actuated and secured in place. FIG. 2 is an isometric view showing more detail of an exemplary stabilization system 10.

In one example, the targeted tissue 12 may be the epicardium of the patient's heart 14 (e.g., epicardial tissue around one or more pulmonary veins), however, the stabilization system 10 may find application in connection with procedures of various cardiac tissues. Access to the heart 14 may be gained through the intercostal spacing between the patient's ribs 15 via a minor incision alternatively access can occur via a sub-xiphoid incision near the sternum or other convenient location. The elongate body or elongate member 16 of the catheter is configured to receive and guide the stabilization system 10 with one or more device for carrying out the procedure to the targeted tissue 12.

In exemplary embodiments, the elongate member 16 is about two feet long, so that the elongate member 16 may extend from a target tissue area target tissue area at the distal end of the stabilization system 10 inside the body (e.g., near the heart 14 inside the sternum) to the proximal end of the stabilization system 10 outside of the patient's body (e.g., through the abdomen as shown in FIG. 1*a-b*) where the wiring 20 and tubing 22, 24 can be connected with various systems and devices such as one or more control and/or feedback units, fluid and vacuum control valves, and the like.

In an embodiment, elongate member 16 is fabricated from flexible resilient materials, and preferably fabricated of materials suitable for use in humans, such as various commercial-grade polymers. Suitable polymers include those well known in the art, such as polyurethanes, polyether-block amides, polyolefins, nylons, polytetrafluoroethylene, polyvinylidene fluoride, and fluorinated ethylene propylene polymers, and other conventional materials. However, the elongate member 16 is not limited to being manufactured from any particular type of material.

The elongate member 16 may be pre-positioned in the appropriate location in the heart prior to introducing the stabilization system 10. Accessing the left atrium with the inventive stabilization system can occur endocardially or epicardially (e.g., via a hemostasis valve or assembly coupled to the left atrial appendage). The clinical approach could be and is not limited to as described within this paragraph, in addition: 1) sub-xiphoid, 2) subclavian (superior vena cava) or femoral (inferior vena cava) or other intravascular approach, 3) or via Open Heart Surgery (OHS). To pre-position the elongate member 16 at the appropriate location in the heart 14, a dilator is first fitted through the elongate member 16. In an example of a procedure within the left atrium, the dilator is first inserted into the patient's body and then maneuvered up to the inferior vena cava and into the right atrium. In what is typically referred to as a transseptal approach, the dilator is pressed through the interatrial septum between the right and left atria. A needle may be used here to make an opening for the dilator to pass through. The dilator expands the opening sufficiently so that the elongate member 16 may then be pressed through the opening to gain access to the left atrium and the pulmonary veins. With the elongate member 16 in position, the dilator is removed and the stabilization system 10 may be fed into the lumen of the elongate member 16 and pushed into the left atrium.

The stabilization system 10 may be implemented at the distal end of elongate member 16 (e.g., a catheter). At the proximal end, the stabilization system 10 may be connected via elongate member 16 to other systems and devices (not shown). As used herein and commonly used in the art, the term "distal" is used generally to refer to components located or generally orientated toward the heart or other tissue (the "target tissue area") when the stabilization system 10 is in use. On the other hand, the term "proximal" is used generally to refer to components or portions of the stabilization system 10, such as the handle (not shown) that are located or generally orientated away from or opposite the target tissue area when the stabilization system 10 is in use.

The elongate member 16 is connected on the distal end to a housing 25 of the stabilization system 10, and defines at least one lumen or longitudinal channel between the proximal and distal ends of the elongate member 16. In exemplary embodiments, wiring 20 (FIG. 2) may be fitted through the lumen. For example, wiring 20 may be provided for delivering electrical signals, power or other energy (e.g., ablative energy) from one or more energy sources, circuitry, outside of the patient's body to one or more operating element 18 (FIG. 2), such as one or more imaging elements, ablation elements, sensors, electrodes, and the like or combinations thereof integrated into or coupled to the housing 25 of stabilization system 10 when positioned within the patient's body. It is noted that any number and/or configuration/placement of the operational element 18 may be utilized. It is also noted that the operational element 18 may also include integrated powering electrodes (not shown) which enable the operational element 18 to receive power from the operational element 18 itself rather than from wiring provided via the elongate member 16. Of course the wiring 20 may also be used to communicate other signals between various sensors (e.g., pressure, temperature, optical sensors, etc.) provided at the distal end of the stabilization system 10 with various output or feedback systems connected to the proximal end of the stabilization system 10. These types of sensors and feedback systems are well understood in the art and therefore further explanation is not necessary herein.

Also in exemplary embodiments, tubing 22 may be fitted through the lumen in elongate member 16. The tubing may be used to provide a fluid or gas under positive and/or negative pressure (e.g., suction or a vacuum) to actuate/deactuate the stabilization system 10, as explained in more detail below with reference to operations of the stabilization system 10.

Fluid delivery tubing 24 may also be provided for delivering a saline solution, or other fluid, gel, and/or gas to the target tissue area. For example, a cooling fluid may be provided for cooling the tissue. Or for example, a coupling fluid may be provided for forming a fluid interface between the ablation element and the tissue. Or for example, a fluid/gas may be provided for controllably inflating and/or deflating a member. Other fluid/gas may include a flushing fluid, contrast media, therapeutic substances, or dye injection, etc. Return lines may also be provided (e.g., for removing fluid and/or gas or body fluids from the target tissue area).

The stabilization system 10 functions to secure or anchor the housing 25 adjacent the target area 12 for a medical procedure (e.g., imaging and/or tissue ablation). The operational element 18 along with associated operational electronics, including electrical signal conductors and possibly processing circuits (e.g., filtering, amplification, and other signal conditioning circuitry), along with various feedback devices (e.g., temperature and contact sensors) and associated circuitry, may all be provided in and/or on the housing 25.

The housing 25 may be fabricated of (or coated with) biocompatible materials suitable for use in humans, such as those described above for elongate member 16. Preferably, the housing 25 is a relatively small, low-profile component such that it may be readily inserted into a patient's body using minimally invasive scope-based or port-based surgery techniques. For example, the housing 25 may have a width of approximately 10-12 mm.

The operational element 18 may be pre-mounted in the housing 25, e.g., during manufacture or by the user prior to use. Alternatively, operational element 18 may be placed separately into the patient's body and then associated with the housing 25 inside the patient's body. Such an embodiment enables the use of separate operational elements (e.g., an imaging ablation element and one or more ablative ablation elements) during the procedure. The housing 25 preferably provides at least some spatial and positional control for the operational element 18.

The operational element 18 may be any suitable ablation element depending on the desired use. For example, the ablation element may be an ablative ablation element, an imaging ablation element, etc. In an exemplary embodiment, the operational element 18 is at least one high intensity focused ultrasound (HIFU) element. The HIFU element may be connected via elongate member 16b to an energy source at the proximal end. The HIFU element converts this energy to ultrasound signals which may be emitted to form lesions in tissue at the target area 12.

Other exemplary ablation elements or ablation energy-emitters that are suitable for use with the stabilization system 10 include, but are not limited to, laser, microwave, non-HIFU transducers, cryogenic and radio frequency (RF) devices. As noted above, more than one ablation element may also be used for a single procedure. For example, an acoustic imaging element may be used to image the target area for pre-imaging of the target tissue area, then a plurality of ablation elements may be used to form ablative lesions in the tissue, and then acoustic imaging ablation element may be used for pre- and/or post-procedure imaging of the target tissue area. That is, multiple operational elements may be housed together to avoid the need to insert and remove multiple operational element during the procedure. Or for example, the same operational element may be used for both imaging and lesion formation by controlling the energy output of the ablation element.

It should also be noted that the stabilization system 10 may also implement a wide variety of different sensing means to provide additional feedback (e.g., contact assessment with the tissue) to the user during the procedures. A wide variety of these types of sensors suitable for use with the stabilization system 10 are well known in the art. Exemplary sensors include but are not limited to piezoelectric, pressure, thermistor, thermocouple, or ultrasound sensors. More than one sensor or type of sensor may also be implemented.

Figure 3A:
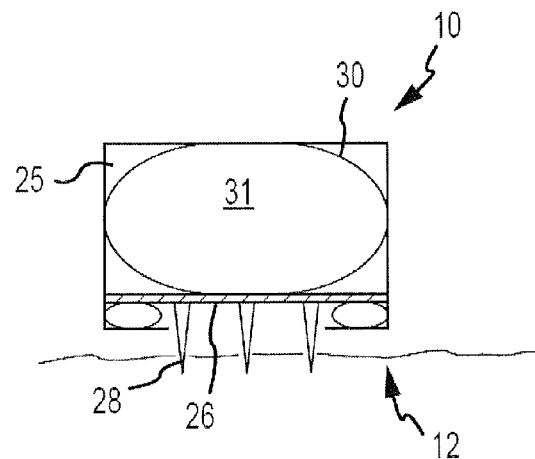
FIG. 3a-b are cutaway rear plan views of the exemplary stabilization system shown in FIG. 2, wherein (a) shows the stabilization system positioned adjacent a target area prior to actuation, and (b) shows the stabilization system after actuation.
Figure 3B:
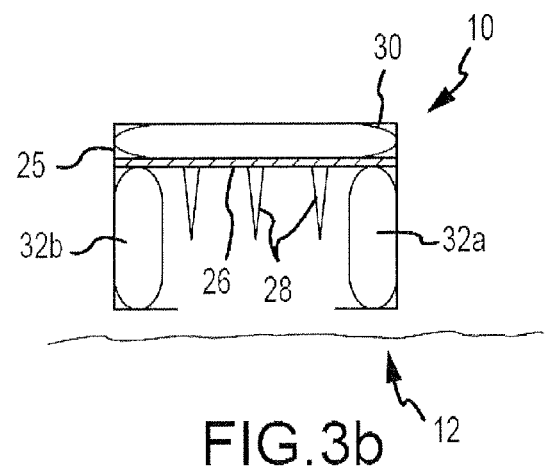

The stabilization system 10 may also include a base portion 26 in housing 25, as better seen in FIG. 3a-b. FIG. 3a-b are cutaway rear plan views of the exemplary stabilization system 10 shown in FIG. 2, wherein (a) shows the stabilization system 10 positioned adjacent a target area 12 prior to actuation, and (b) shows the stabilization system 10 after actuation. One or more securement element 28 may be provided on the base portion 26. During operation, the base portion 26 may be moved in a first direction by expanding membrane 30 so that the securement element 26 engages the tissue 12 (as shown in FIG. 3a) and maintains the housing 25 in a fixed and secure position for a medical procedure. The base portion 26 may be moved in a second direction by contracting the membrane 30 to disengage or release the securement element 28 from the tissue 12 (as shown in FIG. 3b), following the medical procedure or if the housing needs to be moved to another area.

The membrane 30 may be made from conventional materials including urethane (e.g., manufactured by Advanced Polymers Inc., 13 Industrial Way, Salem, N.H. 03079 USA). In an exemplary embodiment, the membrane 30 is provided within the housing 25 and coupled to the elongate member 16 proximate the distal end 24.

The membrane 30 defines an expandable space 31. A fluid or gas may be provided through the elongate member 16 via tubing 22 and into the space 31 to deform the membrane 30 and inflate or expand the space 31 and actuate the stabilization system 10. Likewise, the fluid or gas may be retracted through the elongate member 16 via a vacuum applied to tubing 22 to contract the space 31 and retract the securement element 28 from the tissue 12. In an exemplary embodiment, supplemental membranes 32a-b may be inflated simultaneously in the embodiment of the stabilization system 10' shown in FIG. 3a-b, while deflating membrane 30 in order to assist in retracting the securement element 28 from the tissue 12.

The fluid or gas used for inflating and deflating the membranes 30 and 32a-b may comprise, for example, air (pneumatic fluid), water, cryogenic gas (e.g., nitrous oxide, argon and the like) contrast agent, or a radiopaque solution and combinations wherein membranes 30, 32a, and 32b receive different material. Use of cryogenic gas can provide both the biasing force(s) to stabilize the system 10 via elements 28 to tissue or an organ opposing the targeted tissue and ablation energy for tissue adjacent membrane 30 (e.g., securement 28 engages tissue of the pericardial sac and membrane 30 ablate adjacent epicardial tissue). Use of a contrast agent or radiopaque solution may be particularly useful when employed with fluoroscopy or other imaging procedures to assist the clinician in visualizing the location of the elongate member 16 within the patient's body. Feedback from these procedures may be implemented to better position the stabilization system 10 within the patient's body. The feedback may also be implemented during inflation of the membranes 30 and 32a-b to assist the clinician in gauging the extent of inflation of the membranes 30 and 32a-b so as to provide sufficient pressure to secure the housing 25 against the heart 14 while reducing or altogether eliminating damage to the tissue 12.

It is noted that the housing 25 and base portion 26 of the stabilization system 10 are shown in the figures as being substantially rectangular shaped. It is noted, however, that the housing 25 and base portion 26 may intentionally or unintentionally have a wide variety of configurations, and need not be rectangular-shaped. For example, manufacturing irregularities may result in an elongate and/or non-uniform configuration. Or for example, the housing 25 and base portion 26 may be intentionally selected to have different configurations to achieve desired results. For example, the shape of the base portion 26 corresponds to the configuration of the target tissue area. By way of illustration, the rectangular-shaped base portion 26 shown in the figures may be used to form a substantially linear lesion in the tissue. Alternatively, a curved base portion 26 may be used if it is desired to form a curved lesion. The base portion 26 may also be oval, circular, J-shaped, L-shaped, T-shaped, or any other suitable shape, and the housing 25 may be suitably configured to house the base portion 26. For example, an elongate base portion 26 supporting a plurality of ablation elements can be stabilized as a single unit or with a plurality of membranes 30 and 32a-b to bias the elements toward and stabilize them with respect to an elongate target tissue area thus enabling continuous lesions to be formed. In addition, the base portion 26 and housing 25 can be formed of malleable materials so that they are manually configured to conform to a desired target area. In this form of the invention, the ablation elements can be hinged together and/or spaced apart from each other.

That is, whether or not the base portion 26 includes a plurality of operating elements 18 the base portion 26 may be malleable or flexible so that the base portion 26 conforms to the three-dimensional shape of the tissue. Such flexure reduces gaps between the base portion 26 (and hence the operational element 18) and the tissue 12. This better enables the housing 25 to be anchored to the tissue 12 during use, and also serves to maintain the operational element 18 in good contact (e.g., acoustic coupling) with the adjacent tissue 12. In exemplary embodiments, the base portion 26 may be manufactured of a shape-memory material such as nitinol or a shape-memory polymer so that it automatically returns to an initial state (e.g., for easy removal from the patient's body). Of course, the base portion 26 does not need to be flexible or malleable at all. In other embodiments, the base portion 26 may be stiff and preformed into a desired shape at the manufacturing facility or by force applied by the user.

It is also noted that the known practice of utilizing a fluid-filled acoustically-transparent membrane or standoff between the base portion 26 and the target tissue may also be implemented in order to enhance acoustic coupling of base portion 26 to tissue 12, e.g., to help cool the ablation element and/or even tissues not being ablated at that moment, or to set a desired ablation element working distance to tissue.

In any event, base portion 26 may include one or more securement element(s) 28. The securement element 28 is shown as a plurality of needles. The needles may be solid-core needles, or hollow-core needles (e.g., for delivering a therapeutic fluid to the target tissue 12). It is noted that the securement element 28 may include any suitable means for attaching or anchoring to the tissue 12, and is not limited to the plurality of needles shown in the drawings. In one example, the securement element 28 may include one or more suction port. In such an embodiment, the attachment may be accomplished by suction applied between the base portion 26 and the tissue 12. The suction ports may be spaced substantially evenly around the perimeter of base portion 26, although no such pattern is required. The suction ports may be operatively associated with a vacuum (e.g., a vacuum line provided through elongate member 16). When a vacuum is applied to the suction ports, the base portion 26 attaches to the tissue 12, thereby maintaining a constant position during a procedure. When the vacuum is released, the base portion 26 also releases from the tissue and can be withdrawn from the patient's body in a conventional manner. In another example, the securement element may include a frictional surface. For example, a gel gasket or adhesive may be provided between the base portion 26 and the tissue 12.

Figure 3C:
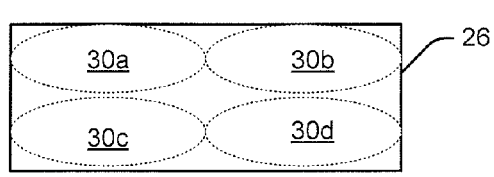
FIG. 3c-d show alternative embodiments of the exemplary stabilization system.
Figure 3D:
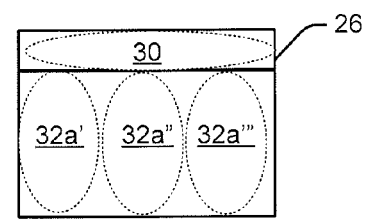

These and other embodiments are also contemplated as suitable attachment means, as will be readily apparent to those having ordinary skill in the art after becoming familiar with the teachings herein. Indeed, the base portion 26 need not be anchored to the target area 12. In other embodiments, the portion of the housing 25 may be disposed over the target area of the tissue so that the base portion 26 opposes the target area 12. That is, although as largely defined above, the base portion 26 is biased toward and/or anchored or otherwise attached adjacent to the target area of the tissue, the base portion 26 can bias away from or anchor on tissue opposing the target area 12. Accordingly, in this form of the invention the housing 25 and membrane 30 can be formed of material that conduct or do not specifically inhibit the ablation energy. The housing 25 and/or base portion 26 can also be controllably raised and lowered, and/or tilted axially or longitudinally in order, for example to change the focal length and/or focal axis of a HIFU ablation element. In addition or in lieu of the foregoing, in order to align and control the operational element 18 for proper imaging and/or so that a quality lesion may be formed diverse size, shape and number of membrane elements 30 and 32a-b can be implemented. For example, FIG. 3c-d show alternative embodiments of the exemplary stabilization system including a plurality of membrane elements 30a-d and 32a', 32a", and 32a'". Thus any mounting tissue located in the target area 12 or opposing and spaced from target area 12 (e.g., tissue area 13) may be utilized as long as it causes the mounted operational element 18 to have the desired spatial relationship with target tissue 12 to accomplish a desired medical procedure (e.g., imaging, sampling, ablating, injecting and/or operating upon the target tissue 12).

Figure 4:
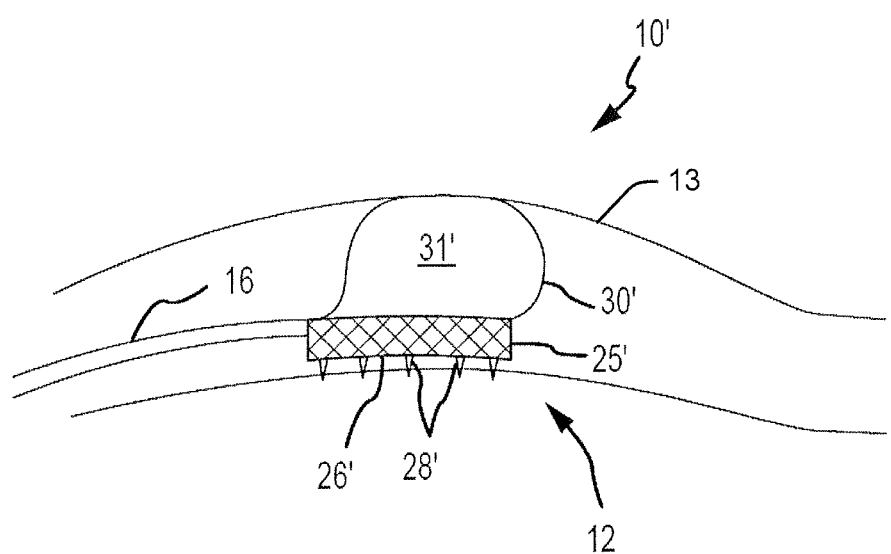
FIG. 4 is a side plan view of another embodiment of an exemplary stabilization system.

FIG. 4 is a side plan view of another embodiment of an exemplary stabilization system 10'. In this embodiment, the membrane 30' may be provided on the exterior of housing 25' of the stabilization system 10'. The membrane 30' may be mounted to the housing 25' by using an adhesive such as ultraviolet (UV) activated biocompatible adhesive or other suitable medical adhesive. The membrane 30' defines an expandable space 31', which may be filled with a fluid or gas to expand and contract the space 31' and actuate/deactuate the stabilization system 10', similarly to the operation described above for stabilization system 10.

FIG. 5 is a cutaway perspective view of another embodiment of an exemplary stabilization system 10". FIG. 6a is a detailed perspective view of an exemplary base portion 26" with edge seal 34 which may be implemented in the stabilization system 10" of FIG. 5. FIG. 6b is a detailed plan view of a needle 36 which may be implemented in the base portion 26" of the stabilization system 10" in FIG. 5.

In this embodiment, an expandable cavity 30" is formed within the housing 25", rather than implementing a membrane to define space 31". A seal 34 is provided around the outside perimeter of the base portion 26". A fluid or gas may be provided through the elongate member 16 via tubing 22 and into the space 31" to move the base portion 26" in the direction of arrow 35a and expand the space 31" within the housing 25", thereby actuating the stabilization system 10. When the space 31" is expanded within the housing 25", the pressure on the base portion 26" also moves securement elements 28" in the direction of arrow 35a and into the tissue 12, as shown in detail in FIG. 6b (see also, FIG. 7b). Likewise, the fluid or gas may be retracted through the elongate member 16 via a vacuum applied to tubing 22 to contract the space 31" and move the base portion 26" in the direction of 35b, thereby removing the securement elements 28" from the tissue 12 (see, e.g., FIG. 7a).

Figure 7A:
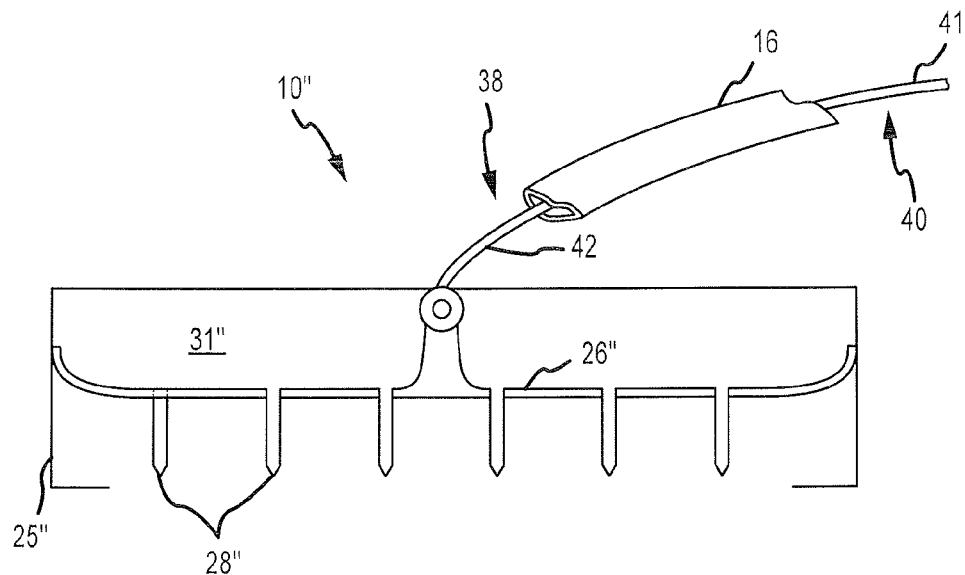
FIG. 7a-b are cutaway side plan views of the embodiment of the stabilization system shown in FIG. 5, wherein (a) shows the safety mechanism in a retracted position, and (b) shows the safety mechanism in a released position.
Figure 7B:
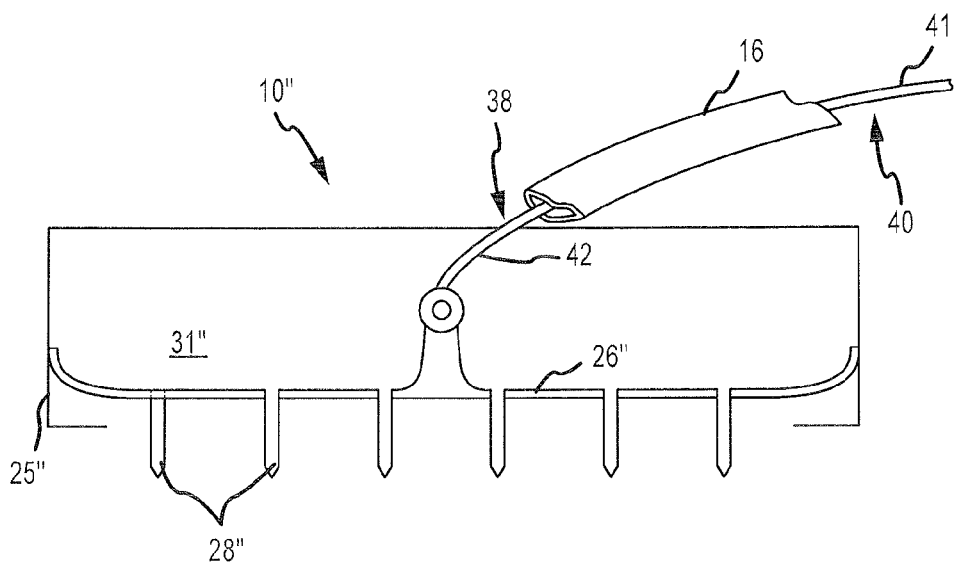

Stabilization system 10" is also shown in FIG. 5 having an exemplary safety mechanism 38. FIG. 7a-b are cutaway side plan views of the embodiment of the stabilization system 10" shown in FIG. 5, wherein (a) shows the safety mechanism 38 in a retracted position, and (b) shows the safety mechanism 38 in a released position.

In an exemplary embodiment, the safety mechanism includes a cable 40 (or cord or the like) provided through the elongate member 16 so that the cable 40 extends outside the patient's body on the proximal end 41, and the cable 40 extending into the housing 25" on the distal end 42 and fixedly attached to the base portion 26". The cable 40 may be operated by applying tension to the cable 40 (e.g., on the proximal end 41 by a technician) to retain the base portion 26" in a closed position (e.g., as shown in FIG. 7a). The cable 40 may also be operated by a locking mechanism (not shown) so that a constant tension is maintained. Accordingly, the base portion 26" is not accidentally released during placement of the housing 25" within, or during removal from, the patient's body. When the housing 25" is properly positioned for a medical procedure, the cable 40 may be released albeit still tethered at a proximal portion of cable 40 (e.g., automatically or by the user) so that the base portion 26" is freely moveable within the cavity 31".

Figure 8:
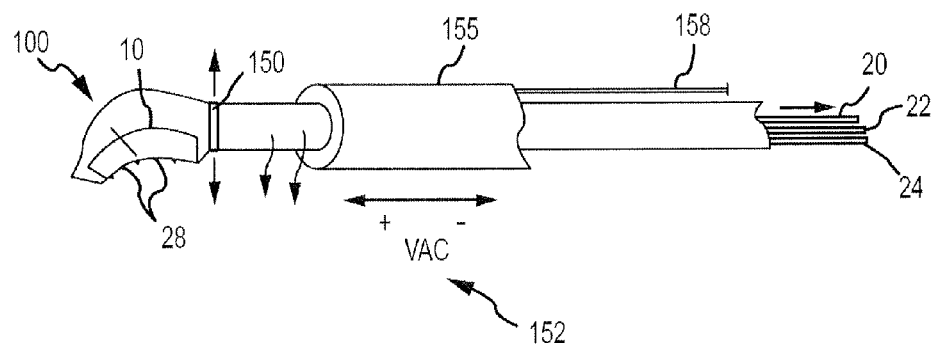
FIG. 8 is an isometric view of another embodiment of an exemplary stabilization system having a collar.

FIG. 8 is an isometric view of another embodiment of an exemplary stabilization system 100 including elements of the stabilization system 10 (or other embodiments such as 10' or 10"), and having a collar 150. As described above, the stabilization system 10 includes securement elements 28 which may be deployed from housing 125, as described above, to secure the housing 125 adjacent the target tissue 12. Collar 150 may also be used, either in the alternative to securement elements 28, or to supplement the attachment of the housing 125 adjacent the target tissue 12.

In one embodiment, the collar 150 is controlled by a vacuum, illustrated by reference 152 in FIG. 8. The positive/negative pressure of the vacuum 152 may be operated by moving a sheath 155 provided within the elongate member 16 (not shown in FIG. 8 for purposes of clarity) toward the distal end to apply positive pressure, and away from the distal end to reduce the pressure. Movement of the sheath 155 may be effected by push/pull rod 158.

Figures 9A, 9C:
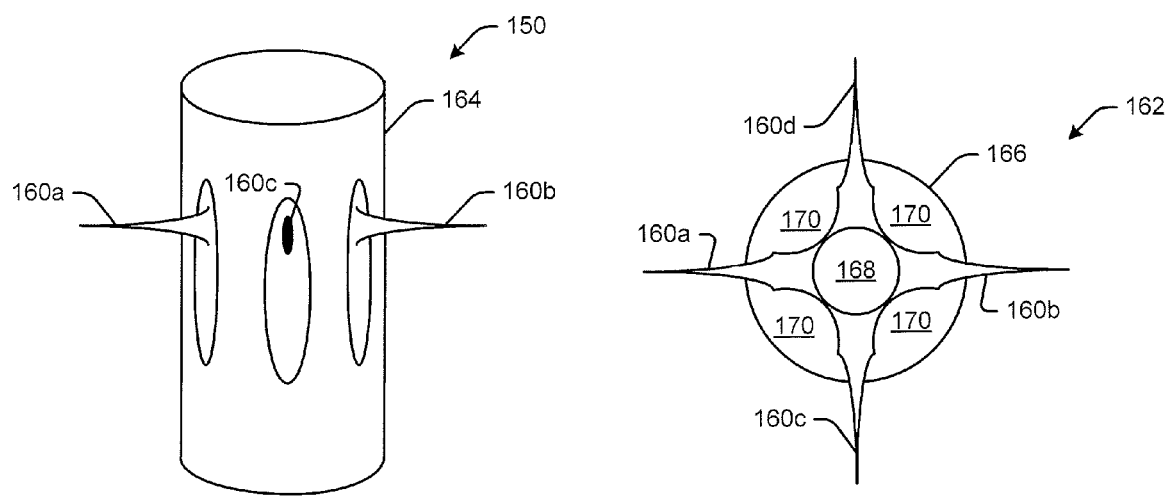
FIG. 9a-c are detailed views of the collar 150 shown in FIG. 8.
Figure 9B:
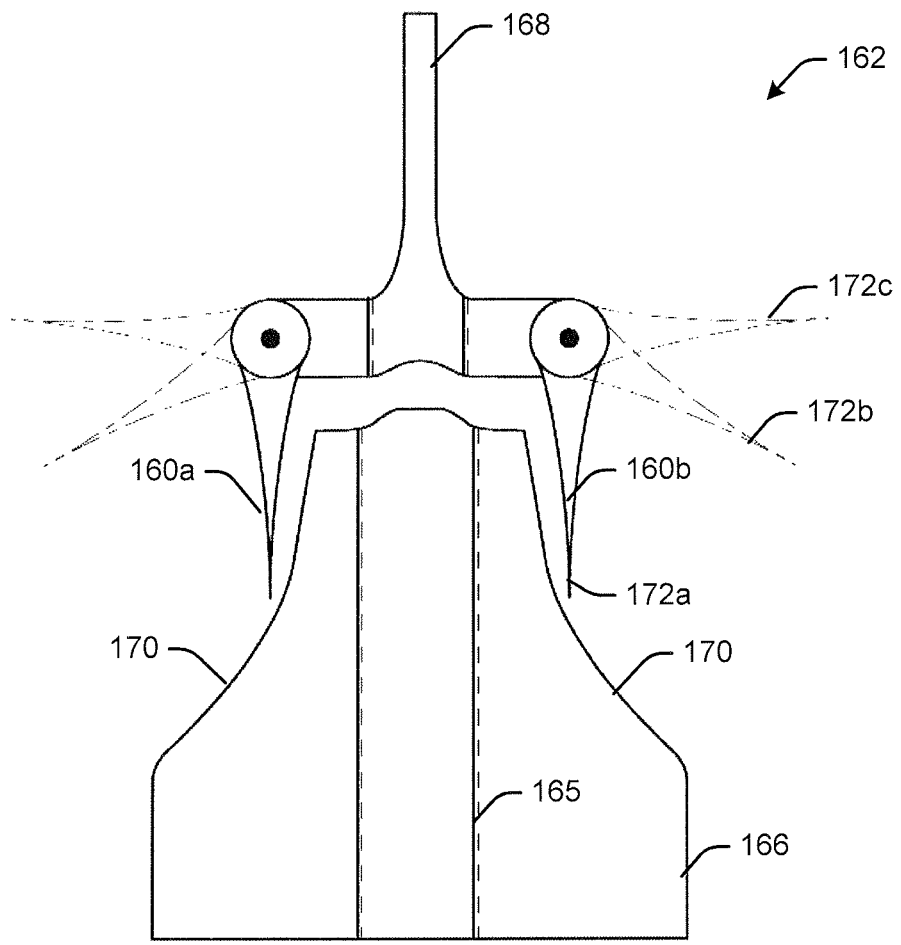

FIG. 9a-c are detailed views of the collar 150 shown in FIG. 8. FIG. 9a is an isometric view of the collar 150 illustrating operation of tissue engaging elements 160 (elements 160a-c are visible in FIG. 9a; elements 160a-b are visible in FIG. 9b; and elements 160a-d are visible in FIG. 9c). The tissue engaging elements 160 may be any suitable engagement means, such as but not limited to, at least one needle, peg, or gasket, to name only a few examples.

In one embodiment, the collar 150 includes an internal activating mechanism 162 to actuate/deactuate the tissue engaging elements 160. FIG. 9b is a cut-away side view of an internal activating mechanism 162. In FIG. 9b, pass-through channel 165 is shown as the channel may be provided to enable wiring or tubing to pass through the collar 150. FIG. 9c is a top view of the internal activating mechanism 162, wherein four engaging elements 160a-d are visible. Although four tissue engaging elements 160 are shown in FIG. 9c, any suitable number of tissue engaging elements 160 may be provided.

In one embodiment, the internal activating mechanism 162 shown in FIGS. 9b and 9c is provided within housing 164 of the collar 150 (as shown in FIG. 9a). The internal activating mechanism 162 includes a base member 166, and a support member 168 moveable relative to the base member 166. The tissue engaging elements 160 may be rotatably mounted on the support member 168. The tissue engaging elements 160 may also be spring-biased in a collapsed position (e.g., position 172a), but rotatable (e.g., through position 172b) to an expanded position (e.g., 172c). The base member 166 has a cam surface 170 formed all around (or substantially around) the base member 166 to effect actuation/deactuation of the tissue engaging elements 160.

In operation, application of positive and negative pressures may be implemented to translate the support member 168 relative to the base member 166. In an exemplary embodiment, pressure lines may be connected adjacent the needle hinges. More specifically, application of a negative pressure (e.g., as described above with reference to FIG. 8) serves as a vacuum on the support member 168 which pulls the support member 168 toward the base member 166. As the support member 168 moves toward the base member 166, the tissue engaging elements 160 come into contact with the cam surface 170 of the base member 166, which causes the tissue engaging elements 160 in the collapsed position (e.g., position 172a) to move outward (e.g., through position 172b) to the deployed position (e.g., position 172c). Application of a positive pressure causes the support member 168 to move away from the base member 166. As the support member 168 moves away from the base member 166, the tissue engaging elements 160 are not longer biased outward by the cam surface 170 of the base member 166, and move inward (e.g., back through position 172b) to the collapsed position (e.g., position 172a).

There are a wide variety of other mechanisms which may also be implemented to translate support member 168 relative to base member 166. By way of example, and without intending to be limiting, support member 168 may translate toward base member 166 by a mechanical force, e.g., by pushing a shaft affixed to the support member 168. In another embodiment, base member 166 may include a cam design that rotates and engages the hinged needles to flare outwards. The cam design may be operated by turning a dial on the catheter handle. Rotating the dial rotates the cam, which engages with the needles 161. Still other designs are also contemplated. For example, electrical actuators may be substituted for the mechanical mechanisms described above.

Although specific designs of stabilization system have been described, other designs of the stabilization system may also be implemented as will be readily understood by those having ordinary skill in the art after becoming familiar with the teachings herein. For example, one or more of the components of stabilization system may be disposable. The particular types and configuration of components used for the stabilization system will depend at least to some extent on design considerations. Exemplary design considerations may include, but are not limited to, the material and desired structural properties, the length, shape, and cross-sectional area of the components. And of course, the design parameters may be different for various procedures or physician preferences.

Having described exemplary embodiments of the stabilization system above, its use will now be described in more detail. During an exemplary procedure, the operational element 18 may be attached in the housing 25 and positioned adjacent the target area 12 or target tissue area. In an exemplary embodiment, the housing 25 may be positioned inside the patient's body using conventional surgical techniques (e.g., the use of scope-based and port-access surgical tools) so that the operational element 18 is positioned at the appropriate location adjacent the target area or target tissue area. Although many applications of the inventive device will be minimally invasive, the present invention may also be used for open surgery procedures.

For purposes of illustration where the target tissue area is tissue on the heart 14, an incision may be made in the patient's body between the ribs, for example, during an MIS procedure. An endoscope may be inserted through the incision and directed toward the heart to visually aid the physician in locating the target tissue area. Once the target tissue area has been located, the housing 25 may be inserted into the patient's body and moved into position.

Once positioned adjacent the target tissue area, the housing 25 may be anchored or otherwise attached to tissue adjacent the target tissue area (e.g., as illustrated in FIG. 1a-b). Although the housing 25 is shown as it may be attached to tissue 12 on the heart 14 surrounding the target tissue area, it has already been noted that in other embodiments the stabilization system 10 may be used to attach to other tissue adjacent the target tissue area (e.g., an opposed tissue surface) so that configuration is not described in detail hereinbelow.

Once the stabilization system 10 has been properly positioned at the desired location (e.g., in the pericardial space located between the pericardial tissue or sac and the epicardial tissue of a heart), the stabilization system 10 may be used to perform various procedures (e.g., imaging, ablation, and other procedures). During operation, the operational element 18 may be actuated for imaging or delivery of ablative or other therapeutic energy to the tissue. For example, a combination imaging-ablation element may be used to pre-scan the target tissue area after placement to help ensure its proper and preferably safe position for the procedure. The imaging-ablation element may then be used to form lesions in the tissue. The imaging-ablation element may be used again to post-scan the target tissue area to ensure the desired lesion has been formed. Of course other ablation elements may also be implemented for a wide variety of different procedures, and the particular use of stabilization system 10 is not limited to the embodiments shown and described herein.

It will be readily appreciated to those having ordinary skill in the art, after becoming familiar with the teaching herein, that the stabilization system enables a wide variety of features and benefits for the user and the patient. For example, having the operational element 18 biased toward, and/or temporarily anchored or otherwise attached adjacent the target tissue area keeps the operational element 18 from moving outside the bounds of the target area. This reduces or altogether eliminates damage to surrounding tissue and helps ensure the user forms quality lesions, such as continuous unbroken extended lesions, a spot lesion or series of spot lesions, or a closed-path lesion. The stabilization system 10 also provides a certain level of control for the user. For example, temporarily fixing the operational element 18 adjacent the target tissue helps ensure that only the desired amount of energy is delivered to the tissue during ablation. The use of imaging or combination imaging-ablation elements also enables the user to visually inspect a target area which may otherwise be difficult to see using conventional imaging techniques such as endoscopes. These, and other features of the stabilization system, are particularly desirable where the tissue may be moving (e.g., the beating heart).

It is noted that the stabilization system 10 has been described as it may be used for procedures in the vicinity of the heart. The stabilization system 10, however, is not limited to such procedures, and may be used for procedures involving other target tissue in other areas of the body.

Although several embodiments of this invention have been described above with a certain degree of particularity, those skilled in the art could make numerous alterations to the disclosed embodiments without departing from the spirit or scope of this invention. References are only used for identification purposes to aid the reader's understanding of the present invention, and do not create limitations as to the position, orientation, or use of the invention. In addition, various combinations of the embodiments shown are also contemplated even if not particularly described. Changes in detail or structure, such as but not limited to combinations of various aspects of the disclosed embodiments, may be made without departing from the spirit of the invention as defined in the appended claims.

What is claimed is:

1. A stabilization system for use in a medical procedure comprising:
   a housing structure having a base portion, the housing structure configured to be inserted into a patient's body;
   a securement element on the base portion of the housing structure;
   a deployment mechanism in the housing structure and operably associated with the base portion, the deployment mechanism including an inflatable deploying membrane and an inflatable retracting membrane, wherein the deploying membrane is inflatable to move the base portion and engage the securement element to a tissue in the patient's body after the housing structure is positioned adjacent a target area inside the patient's body, and wherein the retracting membrane is inflatable to disengage the securement element from the tissue.

2. The system of claim 1, wherein the deployment mechanism includes a sealing structure disposed between an outer perimeter of the base portion and an inner perimeter of the housing structure and configured to form a chamber within the housing structure, wherein the chamber is coupled to one of a source of relatively increased pressure and a source of relatively decreased pressure and said source conveys one of a fluid and a gas.

3. The system of claim 2 wherein the chamber is supplied with increased pressure to engage the securement element to the tissue in the patient's body, and the chamber is supplied with decreased pressure to disengage the securement element from the tissue in the patient's body.

4. The system of claim 1, further comprising a safety mechanism operable to prevent accidental deployment of the securement mechanism.

5. The system of claim 4, wherein the safety mechanism includes a cord attached on one end to the base portion, and wherein the cord is capable of extending outside of the patient's body for activation/deactivation by a user.

6. The system of claim 1, further comprising an operating element disposed within the housing, the operating element selected from the group consisting of an ablation element, an imaging element, a physiologic sensing element, and a combination element for performing at least two of ablation, physiologic sensing, and imaging.

7. The system of claim 6, further comprising an elongate member attached to the ablation element, the elongate member providing a conduit to the ablation element for energy delivery.

8. The system of claim 6, further comprising an elongate member attached to the ablation element, the elongate member providing a conduit to the ablation element for fluid delivery.

9. The system of claim 1, further comprising an elongate member attached to the deployment mechanism, the elongate member providing a conduit to the deployment mechanism for application of relatively increased pressure or relatively decreased pressure.

10. The system of claim 1, wherein the base portion of the housing structure comprises a flexible structure in at least one plane to allow the base to substantially conform to a topography of the tissue during use.

11. The system of claim 1, further comprising a fluid delivery opening in the housing structure, the fluid delivery opening fluidically connected to fluid delivery tubing to deliver fluid to the target area.

12. The system of claim 1, wherein the securement element includes one of: a frictional surface for engaging the tissue, a peg member, and a needle.

13. A stabilization system for use in a medical procedure comprising:
    a housing structure having a base portion, the housing structure configured to be inserted into a patient's body;
    a securement element on the base portion of the housing structure;
    at least one suction port operatively connected to the base portion of the housing structure;
    a deployment mechanism in the housing structure and operably associated with the base portion, the deployment mechanism including an inflatable deploying membrane and an inflatable retracting membrane, wherein the deployment membrane is inflatable to move the base portion so that the at least one suction port engages a tissue in the patient's body after the housing structure is positioned adjacent a target area inside the patient's body, and wherein the retracting membrane is inflatable to disengage the securement element from the tissue.

14. The system of claim 13, wherein the deployment mechanism includes a sealing structure disposed between an outer perimeter of the base portion and an inner perimeter of the housing structure and configured to form a chamber within the housing structure, wherein the chamber is coupled to one of a source of relatively increased pressure and a source of relatively decreased pressure and said source conveys one of a fluid and a gas.

15. The system of claim 13, further comprising an operating element disposed within the housing, the operating element selected from the group consisting of an ablation element, an imaging element, a physiologic sensing element, and a combination element for performing at least two of ablation, physiologic sensing, and imaging.

* * * * *